(12) United States Patent
Ahmed et al.

(10) Patent No.: US 6,221,390 B1
(45) Date of Patent: *Apr. 24, 2001

(54) COMBINATION PHARMACEUTICAL COMPOSITION AND ASSOCIATED METHODS

(75) Inventors: Salah U. Ahmed, New City, NY (US); Gandha Naringrekar, Paramus, NJ (US)

(73) Assignee: Barr Laboratories, Inc., Pomona, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/920,219

(22) Filed: Aug. 25, 1997

(51) Int. Cl.$^7$ ................ A61K 9/64; A61K 9/52; A61K 47/00
(52) U.S. Cl. ............... 424/456; 424/457; 424/490; 514/778; 514/781; 514/960; 514/962
(58) Field of Search ................... 424/457, 490, 424/456; 514/778, 960, 962, 781

(56) References Cited

U.S. PATENT DOCUMENTS

| | | | |
|---|---|---|---|
| 4,255,413 | 3/1981 | Rattie et al. | 424/37 |
| 4,444,769 | 4/1984 | Blume et al. | 424/246 |
| 4,526,777 | 7/1985 | Blume et al. | 424/20 |
| 4,547,498 | 10/1985 | Blume et al. | 424/225 |
| 4,681,765 | 7/1987 | Guley | 424/456 |
| 4,793,999 | 12/1988 | Sheth | 424/451 |
| 4,804,540 | 2/1989 | Nugent et al. | 424/457 |

*Primary Examiner*—Theodore J. Criares
(74) *Attorney, Agent, or Firm*—Mark E. Waddell; Stephen M. Haracz; Bryan Cave LLP

(57) ABSTRACT

A novel pharmaceutical combination is described, together with a method of making the same and a method of treating hypertensive patients using the same, wherein (1) the pharmaceutically active antihypertensive agent and citric acid and (2) the pharmaceutically active antikaliuretic agent and a nonionic surfactant are mixed, either together or separately, to form an essentially homogenous combination composition, and only thereafter blending with excipients to form the novel combination composition in solid dosage form.

28 Claims, No Drawings

COMBINATION PHARMACEUTICAL COMPOSITION AND ASSOCIATED METHODS

BACKGROUND

This invention relates to a novel pharmaceutical composition having an antihypertensive agent and an antikaliuretic agent in combination that provides effective diuretic and hypertensive properties while also being capable of resisting or reversing hypokalemia. In particular, this invention provides a novel pharmaceutical composition having hydrochlorothiazide (6-chloro-3,4-dihydro-2H-1,2,3benzothiadiazine-7-sulfonamide-1,1-dioxide) and triamterene (2,4,7-triamino-6-phenylpteridine) as active ingredients, the composition exhibiting improved dissolution and bioavailability characteristics for both active ingredients.

This invention also relates to an improved method for producing pharmaceutical compositions having two or more active ingredients which differ significantly from each other in their relative hydrophobic and/or hydrophilic and/or physiological characteristics in gastrointestinal fluid.

This invention further relates to an improved method for treating hypertensive patients with a novel pharmaceutical composition having an antihypertensive agent and an antikaliuretic agent in combination that provides effective diuretic and hypertensive properties while also being capable of resisting or reversing hypokalemia.

Currently, a pharmaceutical combination composition having 25 mg hydrochlorothiazide (6-chloro-3,4-dihydro-2H-1,2,3 benzothiadiazine -7-sulfonamide-1,1-dioxide) and 37.5 mg triamterene (2,4,7-triamino-6-phenylpteridine) is being marketed under the Dyazide® (SmithKline Beecham) label. Various granulation methods have been described for the combination pharmaceutical product.

U.S. Pat. No. 4,255,413, Rattle et al., issued Mar. 10, 1981 and U.S. Pat. No. 4,804,540, Nugent et al., issued Feb. 14, 1989 involve using a wet granulation method. This granulation method requires numerous steps, including weighing, mixing, granulation, screening the damp mass, drying, dry screening, and lubrication. Wet granulation processes need an oven or fluid bed to dry at suitable moisture content. Incomplete drying may cause processing problems and may affect stability. Several steps in this method increase the cost for producing a combination pharmaceutical combination. For example, the addition of water to the process requires additional costly validation studies and on-going testing to ensure that the water used therein is microbe and virus-free. Further, the time and energy consumed during the drying step greatly increases the costs associated with this method. Therefore, producing oral dosage forms using a wet granulation method, especially for large scale production, is costly in terms of labor, energy consumed, and time involved.

A melt granulation method incorporating polyethylene glycol ("PEG") into the combination pharmaceutical composition has been described in U.S. Pat. No. 4,793,999, Sheth, issued on Dec. 27, 1988. This process requires heating the batch containing the active ingredients and PEG ("the content") to at least 55° C. in order to fuse the high molecular weight PEG prior to cooling, thereby requiring special equipment such as jacketed mixer or a fluid bed coater capable of heating the content at a desirable temperature, e.g., at least 55° C. The relatively high energy requirement in the melt granulation method increases the costs associated with formulating the desired pharmaceutical composition and the heating process may contribute stability problems. In production scale, the energy requirement makes this method economically disadvantageous.

A slugging or compacting granulation has been described in U.S. Pat. Nos. 4,444,769, Blume et al., issued Apr. 24, 1984; U.S. Pat. No. 4,526,777, Blume et al., issued Jul. 2, 1985; and U.S. Pat. No. 4,547,498, Blume et al., issued Oct. 15, 1985. In this method, each active ingredient and various carriers are weighed, screened, divided into two batches, blended, screened, slugged or compacted, and comminuted using a screen. After being comminuted, the two separate batches are then mixed for final dosage formation. This compaction granulation process requires a special equipment, e.g., roller compactor, for slugging. To achieve desirable results, controlled pressure during slugging is required. For example, excessive pressure may produce hard slugs that may affect the drug release profile. This compaction granulation method requires numerous labor and time-intensive steps that increase costs associated with the formulation.

U.S. Pat. No. 4,681,765, Guley, issued Jul. 21, 1987 describes a mixed granulation method for producing combination pharmaceutical compositions. This method involves a multi-step process wherein water insensitive materials are weighed, dry mixed and wetted using water, resulting in a wet granulation. The wet granulation is then screened and dried to produce a dried granulation. The water sensitive materials are then added as a dry blend to the dried granulation, mixed, screened and blended until uniform. Several steps in this method increase the cost for producing a combination pharmaceutical combination. For example, the addition of water to the process requires additional costly validation studies and on-going testing to ensure that the water used therein is microbe and virus-free. Further, the energy consumed during the drying step greatly increases the costs associated with this method.

What is needed, therefore, is an efficient and cost-effective formulation method for producing a combination pharmaceutical composition containing hydrochlorothiazide and triamterene. The present invention satisfies this need by providing a dry mixing method for producing a hydrochlorothiazide and triamterene combination pharmaceutical composition that, surprisingly, provides acceptable bioavailability and dissolution characteristics using a more economical process.

SUMMARY

The present invention provides, in a presently preferred embodiment, a pharmaceutical composition containing both hydrochlorothiazide and triamterene, particularly in solid dosage form, with the characteristics and properties of acceptable bioavailability, with appropriate absorption of both ingredients, which permits desirable effective diuretic and antihypertensive activity while resisting or reversing hypokalemia.

It is therefore an object of the present invention to provide a safe and effective pharmaceutical composition combining hydrochlorothiazide and triamterene and which is adapted to serve as an antihypertensive and diuretic agent while resisting or reversing hypokalemic side effects.

An additional object of the present invention is to provide a dry mixing formulation method for hydrochlorothiazide and triamterene that provides acceptable bioavailability and dissolution characteristics of the combination composition and is significantly more simple and cost-effective than previously described methods. It is also an object of the present invention to provide a solid dosage unit form produced by a dry mixing formulation method. It is a further object of the present invention to provide treatment of hypertensive patients using a solid dosage unit produced by a dry mixing formulation method.

These and other objects of the present invention will become apparent from the following detailed description.

DETAILED DESCRIPTION

In a preferred embodiment of the present invention, hydrochlorothiazide (6-chloro-3,4-dihydro-2-H-1,2,4-benzothiadiazine-7-sulfonamide 1,1-dioxide) is combined with triamterene (2,4,7-triamino-6-phenylpteridine) and non-toxic pharmaceutically acceptable carriers or other materials to produce the desired dosage form.

A preferred embodiment for the method of manufacturing the combination pharmaceutical composition of the present invention involves the steps of providing respective quantities of triamterene and hydrochlorothiazide at a weight ratio of triamterene to hydrochlorothiazide of about 1.5:1. These ingredients are dry blended together with citric acid and a nonionic surfactant. The blended product is milled and mixed with certain additional dry carrier materials or excipients including a disintegrant, a diluent, a binder, a lubricant, a glidant, and the like that contribute to the desirable characteristics of the present invention. The resulting combination pharmaceutical composition is preferably provided in solid dosage form, particularly as a capsule, or, alternatively, as a tablet.

Another preferred embodiment for the method of manufacturing the combination pharmaceutical composition of the present invention involves the steps of providing respective quantities of triamterene and hydrochlorothiazide at a weight ratio of triamterene to hydrochlorothiazide of about 1.5:1. These ingredients are separately blended and milled. Citric acid and triamterene being admixed together and a nonionic surfactant and hydrochlorothiazide being admixed together. After milling, the above blended products are mixed together and certain additional carrier materials or excipients, including a disintegrant, a diluent, a binder, a lubricant, a glidant, and the like which contribute to the desirable characteristics of the present invention, are then added and mixed with the above mixture. The resulting combination pharmaceutical composition is preferably provided in solid dosage form, particularly as a capsule, or alternatively as a tablet.

The triamterene, USP, ingredient is preferably in dry finely divided form such that about 7% passes through a 200 mesh screen, more preferably about 13% passes through a 200 mesh screen. It may be made up in a mixture containing about 19% (on a triamterene weight basis) of citric acid, powder.

The hydrochlorothiazide, USP, ingredient is preferably in dry finely divided form such that about 50% passes through a 100 mesh screen, more preferably about 70% passes through a 100 mesh. It may be made up in a mixture containing about 32% of a dry nonionic surfactant, preferably poloxamer, NF (188, Pluronic F-68 Prill Surfactant) or an anionic surfactant, e.g., sodium lauryl sulfate.

In one embodiment of the present invention, the two dry active ingredients, triamterene and hydrochlorothiazide, are concomitantly blended and milled with the dry citric acid and the dry nonionic surfactant before additional dry excipients are added thereto.

In another embodiment of the present invention, the triamterene and citric acid are blended and milled separately from the hydrochlorothiazide and the nonionic surfactant. Thereafter, each of these two separately blended and milled mixtures are mixed to form an essentially homogenous blended mixture to which additional excipients are added thereto.

Citric acid is available in both anhydrous and monohydrate forms. Either form may be used.

Additionally, excipients added to the above essentially homogenous mixtures are non-toxic pharmaceutically-acceptable carrier materials. Among the additional excipients that may be included in the above mixtures, all in finely divided and dry form, may be a hydrophillic component such as, preferably, povidone, USP (e.g., Plasdone K-29-32) or povidone with different molecular weight, a disintegrant, e.g., cross-linked polyvinylpyrrolidone NF (as Polyplasdone XL), Croscarmellose sodium (e.g., acdisol), or preferably Sodium starch glycolate NF (e.g., Primojel); a diluent, such as, preferably lactose, dicalcium phosphate, calcium phosphate, starch, microcrystalline cellulose NF (e.g., Avicel® pH 101 or other grades), more preferably-starch and/or microcrystalline cellulose, and most preferably microcrystalline cellulose; a lubricant such as, preferably, talc, aluminum stearate, hydrogenated vegetable oil or stearic acid, NF and most preferably, stearic acid; a glidant or flow enhancer, such as, preferably, silicon dioxide NF, talc, and most preferably colloidal silicon dioxide (e.g.Cab-O-Sil M5). Subsequent to the addition of the excipients, the mixture is then blended and encapsulated or tabletted via any conventional means.

The following examples and data will further illustrate the method of manufacturing, the composition and the method of treatment of the present invention.

Whereas particular embodiments of the invention have been described above for purposes of illustration, it will accordingly be evident to those skilled in the art that numerous variations of the details may be made without departing from the invention as defined in the following claims.

EXAMPLE 1

A capsule formulation, containing 25 mg hydrochlorothiazide and 37.5 mg triamterene was made according to the following procedure using the following materials in the indicated amounts expressed in mg/capsules.

25 mg hydrochlorothiazide, USP; 37.5 mg triamterene, USP; 7.0 mg citric acid (anhydrous); and 8.0 mg poloxamer were mixed for one minute in a high sheer mixer granulator. The resulting essentially homogenous formulation blend was passed through a Hammer mill (Fitz Mill) fitted with a screen 0.0027" openings (no. 1532-0027) with the hammer forward on medium speed. The homogenous formulation blend was then mixed for one minute in the high shear mixer granulator.

Separately, 8.0 mg povidone was passed through a 30 mesh (US Std) screen and then added to the homogenous formulation blend, where the resulting mixture was mixed for thirty seconds. Subsequently and separately, 26.0 mg sodium starch glycolate (Primojel) was passed through the hammer mill (Fitz Mill) fitted with a screen 0.0027" openings (screen no. 1532-0027) and added to the mixture. Further, 10.0 mg lactose monohydrate, NF, together with 38.5 mg Avicel PH 101, NF, were passed through a no. 30 mesh screen and then added to the mixture. The mixture was then mixed for two minutes in a high shear mixer granulator. 3.0 mg stearic acid, NF, and 1.0 mg Cab-O-Sil, NF, were deagglomerated by being passed through a 30 mesh screen. The mixture was then mixed for thirty seconds in a high sheer mixer granulator to form 164 mg of the final formulation product. The final formulation product was then encapsulated using a capsule machine in hard gelatin capsules, size no. 4.

EXAMPLE 2

In order to determine the dissolution characteristics of the present invention composition as compared with a prior, currently-marketed, composition formed of an intimate admixture of hydrochlorothiazide and triamterene, the following in vitro tests were performed. The results were comparable.

| PARAMETER | USP METHOD (TEST I) | USP METHOD (TEST II) | USP METHOD (TEST III) |
|---|---|---|---|
| Medium | 0.1M acetic acid with 1% polysorbate 20 | 4% tetrasodium ethylenediaminetetraacetate, 2% polysorbate 40, 0.05% pancreatin, adjust with phosphoric acid to pH 8.0 ± 0.05 | 0.1N HCL |
| Volume | 900 ml | 900 ml | 900 ml |
| Apparatus | II (Paddle) | I (10 mesh Basket) | I (Basket) |
| Speed | 100 rpm | 100 rpm | 100 rpm |
| Time | 120 mins | 8 hours | 45 minutes |
| Specifications | NLT 80% (Q) in 120 mins. | NLT 70% (Q) in 8 hours for triamterene & NLT 80% (Q) in 8 hours for Hydrochlorothiazide | NLT 75% (Q) in 45 mins. |
| Test Method | UV & HPLC | HPLC | HPLC |

Dissolution Conditions

EXAMPLE 3

A capsule formulation, containing 25 mg hydrochlorothiazide and 37.5 mg triamterene was made according to the following procedure using the following materials in the indicated amounts expressed in mg/capsule. 25 mg hydrochlorothiazide, USP, and 8.0 mg poloxamer, NF were mixed in a high sheer mixer granulator (Collette Gral 10) at low speed with the chopper off for thirty seconds and then passed through a J-Mill fitted with a round hole screen 0.0027" openings (no. 1522-0027) with hammers forward. Separately, 37.5 mg triamterene, USP, and 7.0 mg citric acid, USP, were mixed in a high sheer mixer granulator at low speed with the chopper off for thirty seconds and then passed through a J-Mill fitted with a round hole screen 0.0027" opening with hammers forward. The resulting blends were then mixed together for one minute in a high sheer mixer granulator at low speed with the chopper off to form an essentially homogenous formulation blend. Separately, 8.0 mg povidone was deagglomerated by being passed through a 30 mesh hand screen and then added to the homogenous formulation blend, where the resulting mixture was mixed for thirty seconds in a high sheer mixer granulator at low speed with the chopper off. Subsequently and separately, 26.0 mg Primojel was passed through a J-Mill fitted with a screen (no. 1522-0027) with hammers forward and then added to the mixture. Further, 10.0 mg lactose monohydrate, NF, together with 38.5 mg Avicel PH 101, NF, were deagglomerated by being passed through a no. 30 mesh hand screen and then added to the mixture. The mixture was then mixed for two minutes in a high shear mixer granulator at low speed with the chopper off. 3.0 mg stearic acid, NF, together with 1.0 mg Cab-O-Sil, NF, were deagglomerated by being passed through a no. 30 mesh hand screen. The mixture was then mixed for thirty seconds in a high sheer mixer granulator at low speed with the chopper off to form 164 mg of the final formulation product. The final blend was then encapsulated using a capsule machine (Zanasi LZ 64) in hard gelatin capsules, size no. 4.

EXAMPLE 4

In order to determine the dissolution characteristics of the present invention composition as compared with a prior, currently-marketed, composition formed of an intimate admixture of hydrochlorothiazide and triamterene, in vitro tests were performed using the methods of example 2. The test results were comparable.

EXAMPLE 5

The resulting encapsulated combination pharmaceutical composition containing 25 mg hydrochlorothiazide and 37.5 mg triamterene made according to Example 1, above, may be administered to patients exhibiting hypertension or edema.

The formulation of Example 1 was administered to 39 subjects under fasting condition which produced pharmacokinetic parameters such as Tmax, Cmax and AUC satisfactory for the treatment of edema and hypertension.

EXAMPLE 6

The resulting encapsulated combination pharmaceutical composition containing 25 mg hydrochlorothiazide and 37.5 mg triamterene made according to Example 1, above, may be administered to patients exhibiting hypertension or edema.

The formulation of Example 1 is administered using one or two capsules given once daily, with appropriate monitoring of serum potassium and of the clinical effect.

What is claimed is:

1. A solventless method for producing a pharmaceutical composition having combined pharmaceutically effective diuretic anti-hypokalemic and anti-hypertensive activity comprising:

(a) solventlessly forming an essentially homogenous formulation blend by solventlessly concomitantly blending finely divided particles of triamterene, finely divided particles of hydrochlorothiazide, an enhancing effective amount of citric acid, and a nonionic surfactant and (b) solventlessly mixing the essentially homogenous blend, whereafter the essentially homogenous blend is formulated into s solid unit dosage forms.

2. The method of claim 1 wherein the unit dosage forms are in capsule form containing the thus mixed composition.

3. The method of claim 1, wherein the unit dosage forms are in tablet form containing the thus mixed composition.

4. The method of claim 1, wherein the nonionic surfactant is poloxamer.

5. The method of claim 3, wherein the tablet form further contains a coloring additive.

6. A solid unit dosage formed by the method of claim 1.

7. The solid unit dosage form of claim 6, wherein the unit dosage forms are in capsule form containing the thus mixed composition.

8. The solid unit dosage form of claim 6, wherein the unit dosage forms are in tablet form containing the thus mixed composition.

9. The solid unit dosage form of claim 6, wherein the nonionic surfactant is poloxamer.

10. The solid unit dosage form of claim 8, wherein the tablet form further contains a coloring additive.

11. A method of treating a patient having hypertension using the solid unit dosage form as claimed in claim 6.

12. The method of treating a patient of claim 11, wherein the unit dosage forms are in capsule form containing the thus mixed composition.

13. The method of treating a patient of claim 11, wherein the unit dosage forms are in tablet form containing the thus mixed composition.

14. The method of treating a patient of claim 13, wherein the tablet form further contains a coloring additive.

15. A solventless method for producing a pharmaceutical composition having combined pharmaceutical effective diuretic anti-hypokalemic and anti-hypertensive activity comprising:

(a) solventlessly forming a first mix product by mixing finely divided particles of triamterene and an enhancing effective amount of citric acid, (b) separately solventlessly forming a second mix product by mixing finely divided particles of hydrochlorothiazide and a nonionic surfactant, and (c) solventlessly forming an essentially homogenous formulation blend by concomitantly mixing the first mix product and the second mix product, whereafter the essentially homogenous formulation blend is formulated into solid unit dosage forms.

16. The method of claim 15, wherein the unit dosage forms are in capsule form containing the thus mixed composition.

17. The method of claim 15, wherein the unit dosage forms are in tablet form containing the thus mixed composition.

18. The method of claim 15, wherein the nonionic surfactant is poloxamer.

19. The method of claim 17, wherein the tablet form further contains a coloring additive.

20. A solid unit dosage formed by the method of claim 15.

21. The solid unit dosage form of claim 20, wherein the unit dosage forms are in capsule form containing the thus mixed composition.

22. The solid unit dosage form of claim 20, wherein the unit dosage forms are in tablet form containing the thus mixed composition.

23. The solid unit dosage form of claim 20, wherein the nonionic surfactant is poloxamer.

24. The solid unit dosage form of claim 22, wherein the tablet form further contains a coloring additive.

25. A method of treating a patient having hypertension using the solid unit dosage form as claimed in claim 20.

26. The method of treating a patient of claim 25, wherein the unit dosage forms are in capsule form containing the thus mixed composition.

27. The method of treating a patient of claim 25, wherein the unit dosage forms are in tablet form containing the thus mixed composition.

28. The method of treating a patient of claim 27, wherein the tablet form further contains a coloring additive.

* * * * *